US007312238B2

(12) United States Patent
Chow et al.

(10) Patent No.: US 7,312,238 B2
(45) Date of Patent: *Dec. 25, 2007

(54) NONSEDATING α-2 AGONISTS

(75) Inventors: Ken Chow, Newport Coast, CA (US); Todd M. Heidelbaugh, Fountain Valley, CA (US); John E. Donello, Dana Point, CA (US); Daniel W. Gil, Corona Del Mar, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/458,731

(22) Filed: Jul. 20, 2006

(65) Prior Publication Data
US 2007/0004790 A1    Jan. 4, 2007

Related U.S. Application Data

(63) Continuation of application No. 10/891,953, filed on Jul. 15, 2004, now Pat. No. 7,141,597.

(60) Provisional application No. 60/502,562, filed on Sep. 12, 2003.

(51) Int. Cl.
 *A61K 31/4164* (2006.01)
 *C07D 233/84* (2006.01)
(52) U.S. Cl. .................................. 514/392; 548/325.1
(58) Field of Classification Search .............. 548/325.1; 514/392
See application file for complete search history.

(56) References Cited

U.S. PATENT DOCUMENTS

| 4,798,843 A | 1/1989 | Kruse |
| 4,868,197 A | 9/1989 | Schnettler et al. |
| 7,141,597 B2 * | 11/2006 | Chow et al. ................. 514/392 |

FOREIGN PATENT DOCUMENTS

| EP | 0 284 925 A | 10/1988 |
| EP | 0 302 603 A | 2/1989 |
| JP | 63/150266 A | 6/1988 |
| WO | WO 95/29898 | 11/1995 |

OTHER PUBLICATIONS

Bylund et al, "IV. International Union of Pharmacology Nomenclature of Adrenoceptors", Pharmacol. Rev. 46, No. 2:121-136 (1994).
Hein et al, "Review: Neurotransmitter Receptors IV Adrenergic Receptor Signal Transduction and Regulation", Neuropharmacol. vol. 34, No. 4:357-366 (1995).
Calzada et al, "Alpha-Adrenoceptor Subtypes", Pharmacol. Res. vol. 44, No. 3: 195-208 (2001).
Hein et al, "Gene Substitution/Knockout to Delineate the Role of α2-Adrenoceptor Subtypes in Mediating Central Effects of Catecholaines and Imidazolines", Ann. NY Acad. Science 881: 265-271 (1999).

Ruffolo (Ed.), α-Adrenoreceptors: Molecular Biology, Biochemistry and Pharmacology, 1991)(Cover page only).
Shimizu et al, "A Radioisotopic Method for Measuring the Formation of Adenosine 3', 5'-Cyclic Monophosphate in Incubated Slices of Brain", J. Neurochem. 16: 1609-1619 (1969).
Jasper et al, "Ligand Efficacy and Potency at Recombinant $\alpha_2$ Adrenergic Receptors", Biochem. Pharmacol. 55: 1035-1043 (1998).
Sullivan et al, Measurement of $[Ca^{2+}]$ Using the Fluorometric Imaging Plate Reader (FLIPR), Methods Mol. Biol. 114: 125-133 (1999).
Kao et al, "Photochemically Generated Cytosolic Calcium Pulses and Their Detection by Fluo-3*", J. Biol. Chem. 264: 8179-8184 (1989).
Brandish et al., "Scintillation proximity assay of inositol phosphates in cell extracts: High-throughput measurement of G-protein-coupled receptor activation", Anal. Biochem. 313:311-318 (2003).
Bertrand et al, "The $BRET^2$/Arrestin Assay in Stable Recombinant Cells: A Platform to Screen for Compounds That Interact with G Protein-Coupled Receptors (GPCRS)*", J. Receptor Signal Transduc. Res. 22: 533-541 (2002).
Neve et al, "Dopamine D2 Receptor Stimulation of $Na^+/H^+$ Exchange Assessed by Quantification of Extracellular Acidification", J. Biol. Chem. 267: 25748-25753 (1992).
Lipton et al, "Excitatory Amino Acids as a Final Common Pathway for Neurologic Disorders", New Engl. J. Med. 330: 613-622(1994).
Carelli et al, "Optic nerve degeneration and Mitochondrial dysfunction: genetic and acquired optic neuropathies", Neurochem. Int. 40: 573-584 (2002).
Olichon et al, "Loss of OPA1 Perturbates the Mitochondrial Inner Membrane Structure and Integrity, Leading to Cytochrome c Release and Apoptosis", J. Biol. Chem. 278: 7743-7746 (2003).
Block, "Attention-Deficit Disorder, A Paradigm for Psychotropic Medication Intervention in Pediatrics", Pediatr. Clin. North Am. 45: 1053-1083 (1998).
Pary et al, "Attention Deficit Disorder in Adults", Ann. Clin. Psychiatry 14: 105-111 (2002).
Cordi et al, "Efficient Synthesis of (S)-4(5)-[1-(2,3-Dimethylphenyl)Ethyl]Imidazole Tartrate, The Potent $\alpha_2$ Adrenoceptor Agonist Dexmedetomidine", Synth. Comm. 26: 1585 (1996).
Ciufolini et al, "The Total Synthesis of Cystodytins", J. Amer. Chem. Soc. 113: 8016 (1991).
Horne et al, "A Two-Step Synthesis of Imidazoles from Aldehydes Via 4-Tosyloxazolines", Heterocycles 39: 139-153 (1994).
Hylden et al, "Intrathecal Morphine in Mice: A New Technique", Eur. J. Pharmacol. 67: 313-316 (1980).
Minami et al, "Alloydnia evoked by intrathecal administration of prostaglandin $E_2$ to conscious mice", Pain 57: 217-223 (1994).

* cited by examiner

*Primary Examiner*—Laura L. Stockton
(74) *Attorney, Agent, or Firm*—Brent A. Johnson; Martin A. Voet

(57) ABSTRACT

The present invention provides an α-2A/α-1A selective agonist that includes a compound represented by Structure 1 or a pharmaceutically acceptable salt, ester, amide, sterioisomer or racemic mixture thereof. The present invention further provides a pharmaceutical composition that contains a pharmaceutical carrier and a therapeutically effective amount of an α-2A/α-1A selective agonist that includes a compound represented by Structure 1 or a pharmaceutically acceptable salt, ester, amide, sterioisomer or racemic mixture thereof.

3 Claims, 2 Drawing Sheets

Compound 1

NONSEDATING α-2 AGONISTS

This patent application is a continuation of patent application Ser. No. 10/891,953, filed Jul. 15, 2004 now U.S. Pat. No. 7,141,597 which patent application claims benefit of priority under 35 USC § 119(e) to provisional patent application 60/502,562, filed Sep. 12, 2003, which is hereby incorporated by reference herein.

BACKGROUND OF THE INVENTION

1. Field of the Invention

The invention relates generally to molecular medicine and, more particularly, to α-2 adrenergic agonists that are highly selective for the α-2A adrenergic receptor as compared to the α-1A adrenergic receptor.

2. Background Information

A variety of conditions can be mediated, at least in part, by the sympathetic nervous system including a variety of conditions associated with stress. Sympathetically-enhanced conditions include, without limitation, sensory hypersensitivity such as sensory hypersensitivity associated with fibromyalgia or headache such as migraine; gastrointestinal diseases such as irritable bowel syndrome and dyspepsia; dermatological conditions such as psoriasis; cardiovascular disorders; tachycardias; disorders of peripheral vasoconstriction including Raynaud's Syndrome and scleroderma; panic attack; metabolic disorders such as type II diabetes, insulin-resistance and obesity; disorders of muscle contraction including disorders of skeletal muscle contraction, disorders of smooth muscle contraction, spasticity, and disorders of muscle contraction associated with tension-type headache; behavioral disorders such as, but not limited to, over-eating and drug dependence; and sexual dysfunction.

Although α-2 adrenergic agonists have shown promise in treating symptoms of sympathetically-enhance conditions, use of these α-2 adrenergic agonists can be unsatisfactory due to concomitant sedative effects. This same problem limits effective α-2 adrenergic agonist treatment of other conditions including neurological conditions, ocular conditions and chronic pain. Thus, there is a need for novel effective, non-sedating α-2 adrenergic agonists for use as therapeutics. The present invention satisfies this needs and provides related advantages as well.

SUMMARY OF THE INVENTION

The present invention provides an α-2A/α-1A selective agonist that includes a compound represented by

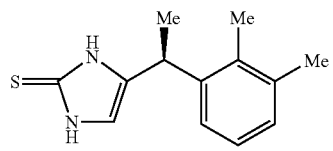

or a pharmaceutically acceptable salt, ester, amide, sterioisomer or racemic mixture thereof. The present invention further provides a pharmaceutical composition that contains a pharmaceutical carrier and a therapeutically effective amount of an α-2A/α-1A selective agonist that includes a compound represented by

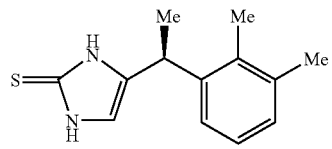

(STRUCTURE 1) or a pharmaceutically acceptable salt, ester, amide, sterioisomer or racemic mixture thereof.

DETAILED DESCRIPTION OF THE INVENTION

Adrenergic receptors mediate physiological responses to the catecholamines, norephinephrine and epinephrine, and are members of the superfamily of G protein-coupled receptors having seven transmembrane domains. These receptors, which are divided pharmacologically into α-1, α-2 and β-adrenergic receptor types, are involved in diverse physiological functions including functions of the cardiovascular and central nervous systems. The α-adrenergic receptors mediate excitatory and inhibitory functions: α-1 adrenergic receptors are typically excitatory post-synaptic receptors which generally mediate responses in the effector organ, while α-2 adrenergic receptors are located postsynaptically as well as presynaptically, where they inhibit release of neurotransmitters. Agonists of α-2 adrenergic receptors currently are used clinically in the treatment of hypertension, glaucoma, spasticity, and attention-deficit disorder, in the suppression of opiate withdrawal, as adjuncts to general anesthesia and in the treatment of cancer pain.

α-2 adrenergic receptors are presently classified into three subtypes based on their pharmacological and molecular characterization: α-2A/D (α-2A in human and α-2D in rat); α-2B; and α-2C (Bylund et al., *Pharmacol. Rev.* 46:121-136 (1994); and Hein and Kobilka, *Neuropharmacol.* 34:357-366 (1995)). The α-2A and α-2B subtypes can regulate arterial contraction in some vascular beds, and the α-2A and α-2C subtypes mediate feedback inhibition of norepinephrine release from sympathetic nerve endings. The α-2A subtype also mediates many of the central effects of α-2 adrenergic agonists (Calzada and Artiñano, *Pharmacol. Res.* 44: 195-208 (2001); Hein et al., *Ann. NY Acad. Science*

881:265-271 (1999); and Ruffolo (Ed.), α-*Adrenoreceptors: Molecular Biology, Biochemistry and Pharmacology* S. Karger Publisher's Inc. Farmington, Conn. (1991)).

Figure 1:
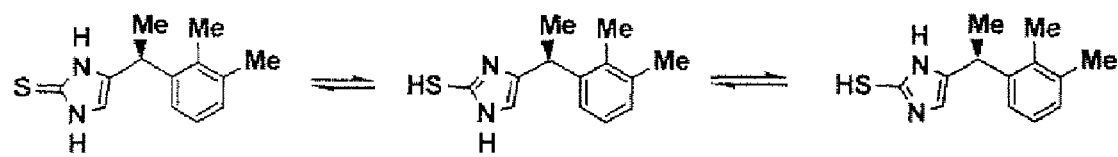
FIG. 1 shows Compound 1 ((+)-(S)-4-[1-(2,3-dimethyl-phenyl)-ethyl]-1,3-dihydro-imidazole-2-thione) from (+)-(S)-4-[1-(2,3-dimethyl-phenyl)-ethyl]-1H-imidazole.

As disclosed herein, several α-2 agonists were assayed for α-2A/α-1A functional selectivity using in vitro cell-based assays. Example I discloses preparation of the α-2 adrenergic agonist ((+)-(S)-4-[1-(2,3-dimethyl-phenyl)-ethyl]-1,3-dihydro-imidazole-2-thione) from (+)-(S)-4-[1-(2,3-dimethyl-Phenyl)-ethyl]-1H-imidazole (see, also, FIG. 1). As shown in Table 1, this α-2 adrenergic agonist, denoted Compound 1, was highly α-2A/α-1A selective, as evidenced by the undetectable level of α-1A activity observed for this compound in a cell-based functional assay (see, also, Example II). In contrast, dexmeditomidine was less α-2A/α-1A selective than was brimonidine (see Table 1). These results indicate that Compound 1 is highly selective for activation of the α-2A receptor as compared to the α-1A receptor.

TABLE 1

α-1A relative efficacy and α-1A/α-2A potency ratios of several α-2 agonists

| Compound | α-1A rel. eff* | α-1A/α-2A pontency ratio |
|---|---|---|
| Brimonidine | 0.2 | 744 |
| Dexmeditomidine | 0.5 | 539 |
| Compound 1 | NA | — |
| Compound 2 | 0.3 | 930 |

*Efficacy relative to the reference full agonist, phenylephrine.
NA = not active As further disclosed herein in Example II, the α-2A/α-1A functional selectivity exhibited in in vitro cell-based assays correlated inversely with in vivo sedative activity at the therapeutic dose. As revealed in FIG. 2, the α-2 agonist which was most highly selective for α-2A/α-1A function in vitro also exhibited the greatest separation between the therapeutic dose which alleviated sulprostone-induced tactile sensitivity and dose resulting in significant sedation. In particular, Compound 1, administered orally at a dose of 1 μg/kg, produced a 50% reduction in sensitization (solid line, left axis), with less than 30% sedation (open diamond, right axis) at doses 100-fold and even 1000-fold greater than the 1 μg/kg therapeutically effective dose (see FIG. 2, lower left panel). This separation between therapeutically effective and sedative doses was greater than that observed for any other α-2 agonist assayed. These results indicate that α-2A/α-1A adrenergic receptor selectivity of α-2 agonists defined using in vitro, cell-based functional assays is inversely correlated with sedative activity at therapeutic doses in vivo following systemic or other peripheral dosing. These results further indicate that particularly useful α-2 agonists, with wide separation between therapeutically effective and sedative doses, are those exhibiting α-2A/α-1A adrenergic receptor functional selectivity.

Based on these discoveries, the present invention provides an α-2A/α-1A selective agonist that includes a compound represented by

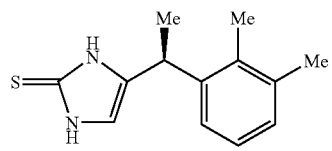

(STRUCTURE 1) or a pharmaceutically acceptable salt, ester, amide, sterioisomer or racemic mixture thereof. A selective agonist of the invention can have, for example, an α-1A efficacy less than that of brimonidine or a ratio of α-1A/α-2A potency greater than that of brimonidine. In one embodiment, an α-2A/α-1A selective agonist of the invention includes a compound represented by FORMULA 1.

An "α-2A/α-1A selective agonist" of the invention can be characterized, in part, by (1) having greater than 25% efficacy relative to brimonidine at one or more α-2 adrenergic receptors including the α-2A adrenergic receptor and (2) further having an α-1A efficacy less than that of brimonidine or a ratio of α-1A/α-2A potency greater than that of brimonidine. In particular embodiments, an α-2A/α-1A selective agonist of the invention has an α-1-A/α-2A $EC_{50}$ ratio which is at least two-fold greater than the α-1A/α-2A $EC_{50}$ ratio of brimonidine, or an α-1A/α-2A $EC_{50}$ ratio which is at least five-fold, ten-fold, twenty-fold, thirty-fold, forty-fold, fifty-fold sixty-fold, seventy-fold, eighty-fold, ninety-fold or 100-fold greater than the α-1A/α-2A $EC_{50}$ ratio of brimonidine. It is understood that, in addition to α-2A agonist activity, an α-2A/α-1A selective agonist of the invention may optionally have agonist or antagonist activity at one or more additional adrenergic or other receptors, provided that the selective agonist satisfies the criteria set forth above in regard to α-2A/α-1A selectivity.

Efficacy, also known as intrinsic activity, is a measure of maximal receptor activation achieved by an agent. For the purposes of determining α-2A/α-1A selectivity, efficacy is preferably determined using any functional assay that does not significantly amplify receptor response. Efficacy can be represented as a ratio or percentage of the maximal effect of the agent to the maximal effect of a standard agonist for each receptor subtype. Brimonidine (UK14304) generally is used as the standard agonist for the α-2A, α-2B and α-2C receptors and is used as the standard herein where relative efficacy of an α-2 receptor is defined. Phenylephrine is an accepted standard agonist for the α-1A, α-1B and α-1D receptors and is used herein as the standard where relative efficacy of an α-1 receptor is defined.

In functionally characterizing an α-2A/α-1A selective agonist of the invention, α-1A efficacy or the ratio of α-1A/α-2A potencies, or both, are compared to that of brimonidine. As used herein, the term "brimonidine" means a compound having the formula that

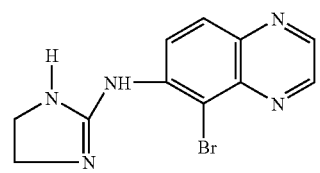

or a pharmaceutically acceptable derivative thereof. The term brimonidine encompasses, without limitation, 5-bromo-6-(2-imidazolin-2-ylamino)quinoxaline D-tartrate (1:1), Alphagan™ and UK14304. Brimonidine, and pharmaceutically acceptable derivatives thereof can be purchased from commercial sources or prepared by routine methods, for example, as described in U.S. Pat. No. 6,323, 204.

Any of a variety of assays are useful to determine α-2A/α-1A functional selectivity. As non-limiting examples, potency, activity or $EC_{50}$ at an α-2A receptor can be determined by assaying for inhibition of adenylate cyclase activity. Furthermore, inhibition of adenylate cyclase activity can be assayed, without limitation, in PC12 cells stably expressing an α-2A receptor such as a human α-2A receptor. As further non-limiting examples, potency, activity or $EC_{50}$ at an α-1A receptor can be determined by assaying for intracellular calcium. Intracellular calcium can be assayed, without limitation, in HEK293 cells stably expressing a α-1A receptor such as a bovine α-1A receptor.

Thus, it is understood that α-2A/α-1A functional selectivity can be characterized using any or a variety of routine functional assays, for example, in vitro cell-based assays which measure the response of an agent proximal to receptor activation. Useful assays include, without limitation, in vitro assays such as cyclic AMP assays or GTPγS incorporation assays for analyzing function proximal to α-2 receptor activation (Shimizu et al., *J. Neurochem.* 16:1609-1619 (1969); Jasper et al., *Biochem. Pharmacol.* 55: 1035-1043 (1998); and intracellular calcium assays such as FLIPR assays and detection of calcium pulses by fluo-3 for analyzing function proximal to α-1 receptor activation (Sullivan et al., *Methods Mol. Biol.* 114:125-133 (1999); Kao et al., *J. Biol. Chem.* 264:8179-8184 (1989)). α-2A selectivity assays based on inhibition of forskolin-induced cAMP accumulation in PC12 cells stably expressing an α-2A receptor, and increases in intracellular calcium in HEK293 cells stably expressing an α-1A receptor, are disclosed herein in Example II below. Additional useful assays include, without limitation, inositol phosphate assays such as scintillation proximity assays (Brandish et al., *Anal. Biochem.* 313:311-318 (2003); assays for β-arrestin GPCR sequestration such as bioluminescence resonance energy transfer assays (Bertrand et al., *J. Receptor Signal Transduc. Res.* 22:533-541 (2002)); and cytosensor microphysiometry assays (Neve et al., *J. Biol. Chem.* 267:25748-25753 (1992)). These and additional assays for proximal α-2 and α-1 receptor function are routine and well known in the art.

As another non-limiting example, a GTPγS assay is an assay useful for determining α-2A/α-1A functional selectivity. α-2 adrenergic receptors mediate incorporation of guanosine 5'-O-(gamma-thio) triphosphate ([$^{35}$S]GTPγS) into G-proteins in isolated membranes via receptor-catalyzed exchange of [$^{35}$S]GTPγS for GDP. An assay based on [$^{35}$S]GTPγS incorporation can be performed essentially as described in Jasper et al., supra, 1998. Briefly, confluent cells treated with an agent to be tested are harvested from tissue culture planes in phosphate buffered saline before centrifuging at 300×g for five minutes at 4° C. The cell pellet is resuspended in cold lysis buffer (5 mM Tris/HCl, 5 mM EDTA, 5 mM EGTA, 0.1 mM PMSF, pH 7.5) using a Polytron Disrupter (setting #6, five seconds), and centrifuged at 34,000×g for 15 minutes at 4° C. before being resuspended in cold lysis buffer and centrifuged again as above. Following the second wash step, aliquots of the membrane preparation are placed in membrane buffer (50 mM Tris/HCl, 1 mM EDTA, 5 mM MgCl2, and 0.1 mM PMSF, pH 7.4) and frozen at −70° C. until used in the binding assay.

GTPγS incorporation is assayed using [$^{35}$S]GTPγS at a specific activity of 1250 Ci/mmol. Frozen membrane aliquots are thawed and diluted in incubation buffer (50 mM Tris/HCl, 5 mM MgCl2, 100 mM NaCl, 1 mM EDTA, 1 mM DTT, 1 mM propranolol, 2 mM GDP, pH 7.4) and incubated with radioligand at a final concentration of 0.3 nM at 25° C. for 60 minutes. After incubation, samples are filtered through glass fiber filters (Whatman GF/B, pretreated with 0.5% bovine serum albumin) in a 96-well cell harvester and rapidly washed four times with four mls of ice-cold wash buffer (50 mM Tris/HCl, 5 mM $MgCl_2$, 100 mM NaCl, pH 7.5). After being oven dried, the filters are transferred to scintillation vials containing five mls of Beckman's Ready Protein® scintillation cocktail for counting. The $EC_{50}$ and maximal effect (efficacy) are then determined for the α-2A receptor.

It is understood that useful assays generally are performed using cells that naturally express significant levels of only a single α-adrenergic receptor subtype or using transfected cells that express significant levels of only a single recombinant α-adrenergic receptor subtype. As a non-limiting example, the adrenergic receptor can be a human receptor or homolog thereof having a similar pharmacology. As disclosed herein, α-2A/α-1A selectivity is preferably determined with receptor-proximal assays, i.e. those in which receptor response is unamplified or amplified only minimally or those in which a rapid signal is assayed. In view of the above, one skilled in the art will prefer to use assays other than Receptor Selection and Amplification Technology (RSAT) assays and similar assays in which partial and full agonism are not well differentiated.

A pharmaceutically acceptable salt, ester, amide, sterioisomer or racemic mixture of Compound 1 can be prepared by routine methods. The α-2A/α-1A selective agonist shown by Structure 1 is merely exemplary of a variety of salts, esters, amides, etc. of this compound that can be readily prepared by one skilled in the art in a similar manner as that disclosed herein using well known methods of chemical synthesis, including methods similar to those exemplified herein (see Example I).

One skilled in the art understands that, in addition so the synthetic scheme shown in Example I, a variety of routes can be used to prepare, for example, the imidazole ring system of Compound 1. Such syntheses are well known in the art, as described, for example, in Grimmett, "Imidazole and Benzimidazole Synthesis," Ross Academic Press (1997). Furthermore, alternative routes for producing imidazole-2-thiones from imidazoles also can be useful in preparing the selective agonist of Compound 1. As a non-limiting example, the imidazole-2-thione ring system can be prepared from an imidazole ring by selectively protecting the N1 nitrogen by a trityl group, followed by deprotonation with a strong base such as n-BuLi or LDA to form the anion at C2. The anion can subsequently be reacted with sulfur to give the desired imidazole-2-thione. As a further non-limiting example, an imidazole ring can be reacted with phenylchloroformate to produce 2-imidazolone, which can be converted to the thione, for example, using Lawesson's reagent. These and similar methods are well known in the art for preparation of Compound 1 and other α-2A/α-1A selective agonists of the invention.

An α-2A/α-1A selective agonist provided herein can be useful, for example, for prevention or alleviation of a sympathetically-enhanced condition without concomitant sedation upon peripheral administration. Any of a variety of sympathetically-enhanced conditions can be prevented or alleviated without concomitant sedation by an α-2A/α-1A selective agonist of the invention, including, without limitation, sensory hypersensitivity such as that associated with fibromyalgia or headaches such as migraines; gastrointestinal diseases such as irritable bowel syndrome and dyspepsia; dermatological conditions such as psoriasis; cardiovascular disorders; tachycardias; disorders of peripheral vasoconstriction including Raynaud's Syndrome and scleroderma; panic attacks; metabolic disorders such as type II diabetes, insulin-resistance and obesity; disorders of muscle contraction including disorders of skeletal muscle contraction, disorders of smooth muscle contraction, spasticity, and disorders of muscle contraction associated with tension-type headache; behavioral disorders such as, but not limited to, over-eating and drug dependence; and sexual dysfunction.

An α-2A/α-1A selective agonist provided herein also can be useful, for example, for prevention or alleviation of chronic pain without concomitant sedation upon peripheral administration. Chronic pain is a term which means pain other than acute pain and includes, without limitation, neuropathic pain, visceral pain, inflammatory pain, headache pain, muscle pain and referred pain. It is understood that chronic pain is of relatively long duration, for example, several years and can be continuous or intermittent. Chronic pain is distinguished from acute pain, which is immediate, generally high threshold, pain brought about by injury such as a cut, crush, burn, or by chemical stimulation such as that experienced upon exposure to capsaicin, the active ingredient in chili peppers.

Any of a variety of types of chronic pain can be prevented or alleviated without concomitant sedation by an α-2A/α-1A selective agonist of the invention including, but not limited to, neuropathic pain such as neuropathic pain associated with diabetic neuropathy or post-herpetic neuralgia; chronic pain associated with cancer; post-operative pain; allodynic pain such as fibromyalgic pain; chronic pain associated with Complex Regional Pain Syndrome (CRPS); chronic visceral pain such as that associated with irritable bowel syndrome or dysmennorhea; chronic headache pain such as migraine pain, non-vascular headache pain, cluster headache pain or daily tension headache pain; and chronic muscle pain such as, yet not limited to, that associated with back spasm.

An α-2A/α-1A selective agonist provided herein additionally can be useful, for example, for prevention or alleviation of a neurological condition without concomitant sedation upon peripheral administration. Such a neurological condition can be, without limitation, an acute or chronic neurological condition. As non-limiting examples, acute neurological conditions which can be prevented or alleviated without concomitant sedation by an α-2A/α-1A selective agonist of the invention include stroke; head and spinal cord trauma; and seizure. Furthermore, chronic neurological conditions which can be prevented or alleviated without concomitant sedation by an α-2A/α-1A selective agonist of the invention include, but are not limited to, neurodegenerative diseases such as Alzheimer's disease; Parkinson's disease; Huntington's disease; amyotrophic lateral sclerosis and multiple sclerosis; HIV-associated dementia and neuropathy; ocular diseases such as glaucoma, diabetic neuropathy and age-related macular degeneration; and schizophrenia, drug addiction, withdrawal and dependency, and depression and anxiety.

The term neurological condition encompasses all acute and chronic disorders which affect, at least in part, neurons. Thus, the term neurological condition encompasses, without limitation, hypoxia-ischemia (stroke); head and spinal cord injury; epilepsy; neurodegenerative disorders such as Alzheimer's disease, Parkinson's disease, Parkinsonism; Huntington's disease, amyotrophic lateral sclerosis and multiple sclerosis; optic neuropathies such as glaucoma, light-induced retinal degeneration such as photoreceptor degeneration, and macular degeneration; disorders of photoreceptor degeneration such as retinitis pigmentosa; HIV-associated dementia (acquired immunodeficiency syndrome dementia complex) and HIV-associated neuropathy; metabolic, mitochondrial and infectious brain abnormalities such as, but not limited to, encephalitis; neuropathic pain syndromes such as causalgia or painful peripheral neuropathies; olivopontocerebellar atrophy; mitochondrial abnormalities and other biochemical disorders such as MELAS syndrome, MERRF, Leber's disease, Wernicke's encephalopathy, Rett syndrome, homocysteinuria, hyperhomocysteinemia, hyperprolinemia, nonketotic hyperglycinemia, hydroxybutyric aminoaciduria, sulfite oxidase deficiency, combined systems disease, lead encephalopathy; hepatic encephalopathy, Tourette's syndrome; drug addiction and drug dependency; drug withdrawal such as withdrawal from alcohol or opiates; and depression or anxiety syndromes (see, for example, Lipton and Rosenberg, *New Engl. J. Med.* 330: 613 (1994)).

An α-2A/α-2A selective agonist provided herein further can be useful, for example, for prevention or alleviation of an ocular condition without concomitant sedation upon peripheral administration. Ocular conditions to be prevented or alleviated without concomitant sedation by an α-2A/α-1A selective agonist of the invention include, without limitation, glaucoma; macular degeneration; and retinopathies such as diabetic retinopathy.

Any of a variety of ocular conditions can be prevented or alleviated without concomitant sedation following peripheral administration of an α-2A/α-1A selective agonist of the invention. Such conditions include, yet are not limited to, diabetic retinopathy; macular edema such as that associated with diabetes; conditions of retinal degeneration such as glaucoma, macular degeneration such as age-related macular degeneration (ARMD) and retinitis pigmentosa; retinal dystrophies; inflammatory disorders of the retina; vascular occlusive conditions of the retina such as retinal vein occlusions or branch or central retinal artery occlusions; retinopathy of prematurity; retinopathy associated with blood disorders such as sickle cell anemia; elevated intraocular pressure; ocular itch; damage following retinal detachment; damage or insult due to vitrectomy, retinal or other surgery; and other retinal damage including therapeutic damage such as that resulting from laser treatment of the retina, for example, pan-retinal photocoagulation for diabetic retinopathy or photodynamic therapy of the retina. Ocular conditions that can be prevented or alleviated without concomitant sedation by peripheral administration of an α-2A/α-1A selective agonist of the invention further include, without limitation, generic and acquired optic neuropathies such as optic neuropathies characterized primarily by loss of central vision, for example, Leber's hereditary optic neuropathy (LEON), autosomal dominant optic atrophy (Kjer disease) and other optic neuropathies such as those involving mitochondrial defects aberrant dynamin-related proteins or inappropriate apoptosis; and optic neuritis such as that associated with multiple sclerosis, retinal vein occlusions or photodynamic or laser therapy. See, for example, Carelli et al., *Neurochem. Intl.* 40:573-584 (2002); and Olichon et al., *J. Biol. Chem.* 278:7743-7746 (2003). It is understood that these and other ocular abnormalities, especially those of the neurosensory retina, can be prevented or alleviated without concomitant sedation using the selective agonists of the invention.

In addition to preventing or alleviating sympathetically-enhanced conditions, neurological conditions, ocular conditions and chronic pain, an α-2A/α-1A selective agonist can be useful for preventing or alleviating other disorders without concomitant sedation. Such a disorder can be, for example, attention deficit disorder (ADHD/ADD), which is a disorder primarily characterized by inattention, distractibility and impulsiveness starting before the age of seven. Symptoms can include, without limitation, fidgeting and squirming, difficulty in remaining seated, easy distractability, difficulty awaiting one's turn, difficulty in refraining from blurting out answers, inability to follow instructions, excessive talking, and other disruptive behavior (Anderson, supra, 1994). Furthermore, while originally recognized in children, ADHD/ADD continues into adulthood in many individuals (see, for example, Block, *Pediatr. Clin. North Am.* 45:1053-1083 (1998); and Pary et al., *Ann. Clin. Psychiatry* 14:105-111 (2002)). One skilled in the art understands that a method of the invention can be useful for preventing or alleviating ADHD/ADD in children and adults having mild as well as severe forms of the disorder.

An α-2A/α-1A selective agonist also can be useful to prevent or alleviate nasal congestion; diarrhea; urinary disorders such as hyperactive micturition and overactive bladder; congestive heart failure; or a psychosis such as a manic disorder. Furthermore, an α-2A/α-1A selective agonist can be useful to prevent or alleviate one or more symptoms associated with anesthesia such as nausea, vomiting, shivering or panic; or to enhance memory and cognitive processes, without concomitant sedation.

As disclosed herein, an α-2A/α-1A selective agonist of the invention is characterized, in part, by the ability to prevent or alleviate any of a variety of sympathetically-enhanced conditions, neurological conditions, ocular conditions and types of chronic pain without concomitant sedation. The term "alleviating," as used herein, means reducing by at least about 50% at least one symptom of the particular condition or type of chronic pain being treated.

Figure 2:
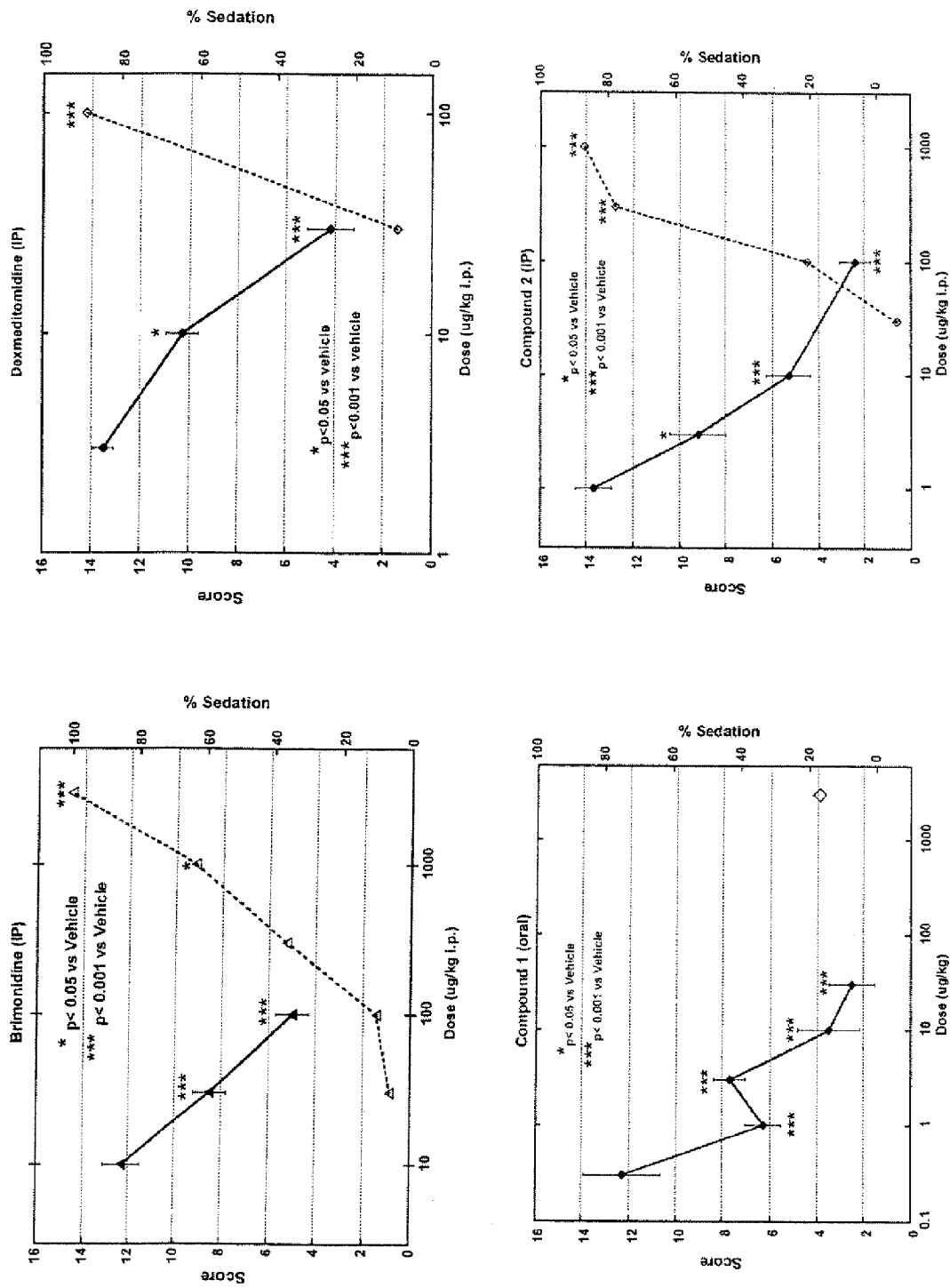
FIG. 2 shows that Compound 1 is superior to brimonidine in its ability to alleviate sulprostone-induced tactile hypersensitivity in the absence of sedation. The dose-responsive anti-hypersensitive and sedative effects of four α-2 agonists were compared in models of sulprostone-induced tactile hypersensitivity and locomotor activity. Upper left panel: I.P. Brimonidine. Upper right panel: I.P. Dexmeditomidine. Lower left panel: Oral Compound 1. Lower right panel: I.P. Compound 2. The mean total sensitivity score and standard error of the mean were calculated (see solid line and solid symbols, left axis). Locomotor activity relative to vehicle-treated animals was expressed as a percentage, and the percent sedation calculated as 100% minus the percent locomotor activity (see hatched line and open symbols, right axis).

As is well known in the art, sedation is a term that means a reduction in motor activity. The phrase "without concomitant sedation," as used herein in reference to a selective agonist, means that, upon peripheral administration, the selective agonist produces less than about 30% sedation at a dose 10-fold greater than the dose of selective agonist required to produce a 50% reduction of one or more symptoms of the particular condition or type of chronic pain being treated. For example, as shown in FIG. 2 (lower left panel), Compound 1 was administered orally at a dose of 1 μg/kg to produce a 50% reduction in sensitization score (solid line, left axis) with less than 30% sedation (open diamond, right axis) at doses 100-fold and even 1000-fold greater than the 1 μg/kg therapeutically effective dose. Thus, the α-2A/α-1A selective agonist represented by formula Compound 1 has effective therapeutic activity "without concomitant sedation." In contrast, many α-2 agonists such as dexmeditomidine are completely sedating at doses 10-fold greater than the dose required to produce a 50% reduction in sensitization score.

As non-limiting examples, the dose of α-2A/α-1A selective agonist required to produce about 30% sedation (reduction in motor activity) can be at least 25-fold greater than, 50-fold greater than, 100-fold greater than, 250-fold greater than, 500-fold greater than, 1000-fold greater than, 2500-fold greater than, 5000-fold greater than, or 10,000-fold greater than the dose required to produce a 50% reduction in one or more symptoms of the particular condition or type of chronic pain being treated. Methods for determining the extent of a reduction in a symptom as well as the extent of sedation are described herein and further are well known in the art.

The present invention further provides a pharmaceutical composition that contains a pharmaceutical carrier and a therapeutically effective amount of an α-2A/α-1A selective agonist that includes a compound represented by

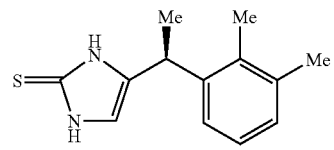

(STRUCTURE 1) or a pharmaceutically acceptable salt, ester, amide, sterioisomer or racemic mixture thereof. In a pharmaceutical composition of the invention, the selective agonist can have, for example, an α-1A efficacy less than that of brimonidine or a ratio of α-1A/α-2A potency greater than that of brimonidine. In one embodiment, the α-2A/α-1A selective agonist of the invention included in a pharmaceutical composition of the invention contains a compound represented by Structure 1.

Thus, the invention provides a pharmaceutical composition containing an effective amount of a pharmaceutical carrier and a therapeutically effective amount of an α-2A/α-1A selective agonist of the invention. Such a pharmaceutical composition can be useful for preventing or alleviating, for example, any of the sympathetically-enhanced, neurological, or ocular conditions or types of chronic pain disclosed herein above without concomitant sedation. A pharmaceutical composition of the invention includes an α-2A/α-1A selective agonist and further includes a pharmaceutically acceptable carrier, which is any carrier, excipient or diluent that has substantially no long term or permanent detrimental effect when administered to a subject. An excipient generally is mixed with an active α-2A/α-1A selective agonist, or permitted to dilute or enclose the selective agonist. A carrier can be a solid, semi-solid, or liquid agent that acts as an excipient or vehicle for the active selective agonist. Examples of solid carriers useful in the pharmaceutical compositions of the invention include, without limitation, pharmaceutical grades of mannitol, lactose, starch, magnesium stearate, sodium saccharin, polyalkylene glycols, talcum, cellulose, glucose, sucrose and magnesium carbonate. Suppository formulations can include, for example, propylene glycol as a carrier. Examples of pharmaceutically acceptable carriers further include, without limitation, water, such as distilled or deionized water; saline; aqueous dextrose, glycerol, ethanol and the like. It is understood that the active ingredients within a pharmaceutical composition can be soluble or can be delivered as a suspension in the desired carrier or diluent.

A pharmaceutical composition can optionally include one or more agents such as, without limitation, emulsifying agents, wetting agents, sweetening or flavoring agents, tonicity adjusters, preservatives, buffers or anti-oxidants. Tonicity adjustors useful in a pharmaceutical composition of the invention include, but are not limited to, salts such as sodium acetate, sodium chloride, potassium chloride, mannitol or glycerin and other pharmaceutically acceptable tonicity adjustors. Preservatives useful in the pharmaceutical compositions of the invention include, without limitation, benzalkonium chloride, chlorobutanol, thimerosal, phenylmercuric acetate, and phenylmercuric nitrate. Various buffers and means for adjusting pH can be used to prepare a pharmaceutical composition, including cut not limited to, acetate buffers, citrate buffers, phosphate buffers and borate buffers. Similarly, anti-oxidants useful in pharmaceutical compositions are well known in the art and includes for example, sodium metabisulfite, sodium thiosulfate, acetylcysteine, butylated hydroxyanisole and butylated hydroxytoluene. It is understood that these and other substances known in the art of pharmacology can be included in a pharmaceutical composition of the invention. See, for example, Remington's *Pharmaceutical Sciences* Mack Publishing Company, Easton, Pa. 16th Edition 1980. It is further understood that a pharmaceutical composition containing an α-2A/α-1A selective agonist can optionally be administered in conjunction with one or more other therapeutic substances, in the same or a different pharmaceutical composition and by the same or different routes of administration.

An α-2A/α-1A selective agonist is peripherally administered to a subject in a therapeutically effective amount. Such a therapeutically effective amount generally is the minimum dose necessary to achieve the desired prevention or alleviation of one or more symptoms of, for example, a sympathetically-enhanced condition, neurological condition, ocular condition or chronic pain, such as that amount roughly necessary to reduce to tolerable levels the discomfort caused by the sympathetically-enhanced condition, neurological condition, ocular condition or chronic pain. Such a dose can be an amount which reduces at least one symptom of the condition or type of pain by at least about 50% and generally is in the range of 0.1-1000 mg/day and can be, for example, in the range of 0.1-500 mg/day, 0.5-500 mg/day, 0.5-100 mg/day, 0.5-50 mg/day, 0.5-20 mg/day, 0.5-10 mg/day or 0.5-5 mg/day, with the actual amount to be administered determined by a physician taking into account the relevant circumstances including the severity and type of sympathetically-enhanced condition, neurological condition, ocular condition or chronic pain; the age and weight of the subject; the subject's general physical condition; and the pharmaceutical formulation and route of administration. As discussed further below, a pharmaceutical composition of the invention also can be useful in the form of a suppository or extended release formulation such as, without limitation, a dermal patch, formulation for deposit on or under the skin, or formulation for intramuscular injection.

In one embodiment, a pharmaceutical composition of the invention is an ophthalmic composition. An ophthalmic composition contains an ophthalmically acceptable carrier, which is any carrier that has substantially no long term or permanent detrimental effect on the eye to which it is administered. Examples of ophthalmically acceptable carriers include, without limitations water, such as distilled or deionized water; saline; and other aqueous media. Ophthalmic compositions can incorporate, for example, soluble α-2A/α-1A selective agonist, or an α-2A/α-1A selective agonist as a suspension in a suitable carrier.

Topical ophthalmic compositions also are useful. Such compositions encompass, without limitation, ocular drops, ocular ointments, ocular gels and ocular creams. Such ophthalmic compositions are easy to apply and deliver the selective agonist effectively. Components of a non-limiting, exemplary topical ophthalmic composition are shown below in Table 2.

TABLE 2

| Ingredient | Amount (% W/V) |
| --- | --- |
| Compound | about 0.0001 to about 0.1 |
| Preservative | 0-0.10 |
| Vehicle | 0-40 |
| Tonicity Adjustor | 1-10 |
| Buffer | 0.01-10 |
| pH Adjustor | q.s. pH 4.5-7.5 |
| antioxidant | As needed |
| Purified Water | As needed to make 100% |

A preservative can be included, if desired, in an ophthalmic composition of the invention. Such a preservative can be, without limitation, benzalkonium chloride, chlorobutanol, thimerosal, phenylmercuric acetate, or phenylmercuric nitrate. Vehicles useful in a topical ophthalmic composition include, yet are not limited to, polyvinyl alcohol, povidone, hydroxypropyl methyl cellulose, poloxamers, carboxymethyl cellulose, hydroxyethyl cellulose and purified water.

A tonicity adjustor also can be included, if desired, in an ophthalmic composition of the invention. Such a tonicity adjustor can be, without limitation, a salt such as sodium chloride, potassium chloride, mannitol or glycerin, or another pharmaceutically or ophthalmically acceptable tonicity adjustor.

Various buffers and means for adjusting pH can be used to prepare anophthalmic composition in the invention, provided that the resulting preparation is ophthalmically acceptable. Such buffers include, but are not limited to, acetate buffers, citrate buffers, phosphate buffers and borate buffers. It is understood that acids or bases can be used to adjust the pH of the composition as needed. Ophthalmically acceptable antioxidants useful in preparing an ophthalmic composition include, yet are not limited to, sodium metabisulfite, sodium thiosulfate, acetylcysteine, butylated hydroxyanisole and butylated hydroxytoluene.

An α-2A/α-1A selective agonist of the invention or a pharmaceutical composition containing such a selective agonist is peripherally administered to a subject. As used herein in reference to an α-2A/α-1A selective agonist, the term "peripherally administering" or "peripheral administration" means introducing the α-2A/α-1A selective agonist into a subject outside of the central nervous system. Thus, peripheral administration encompasses any route of administration other than direct administration to the spine or brain.

A therapeutically effective amount of an α-2A/α-1A selective agonist can be peripherally administered to a subject by any of a variety of means depending, for example, on the type of condition or chronic pain to be prevented or alleviated, the pharmaceutical formulation, and the history, risk factors and symptoms of the subject. Suitable routes of peripheral administration include both systemic and local administration. As non-limiting examples, a therapeutically effective amount of an α-2A/α-1A selective agonist can be administered orally; parenterally; by subcutaneous pump; by dermal patch; by intravenous, intra-articular, subcutaneous or intramuscular injection; by topical drops, creams, gels or ointments; as an implanted or injected extended release formulation; or by subcutaneous minipump or other implanted device.

One skilled in the art understands that peripheral administration can be local or systemic. Local administration results in significantly more of an α-2A/α-1A selective agonist being delivered to and about the site of local administration than to regions distal to the site of administration. Systemic administration results in delivery of an α-2A/α-1A selective agonist essentially throughout at least the entire peripheral system of the subject.

Routes of peripheral administration useful for delivery of an α-2A/α-1A selective agonist or pharmaceutical composition of the invention encompass, without limitation, oral administration, topical administration, intravenous or other injection, and implanted minipumps or other extended release devices or formulations. An α-2A/α-1A selective agonist or pharmaceutical composition of the invention can be peripherally administered, without limitation, orally in any acceptable form such as in a tablet, pill, capsule, powder, liquid, suspension, emulsion or the like; as an aerosol; as a suppository; by intravenous, intraperitoneal, intramuscular, subcutaneous or parenteral injection; by transdermal diffusion or electrophoresis; topically in any acceptable form such as in drops, creams, gels or ointments; and by minipump or other implanted extended release device or formulation. An α-2A/α-1A selective agonist optionally can be packages in unit dosage form suitable nor single administration of precise dosages, or in sustained release dosage form or continuous controlled administration.

Chronic administratation of an α-2A/α-1A selective agonist or pharmaceutical composition of the invention can be useful, for example, for prevention or alleviation of chronic pain or another chronic condition such as, without limitation, a chronic neurological condition. Means for repeated or continuous peripheral administration include, without limitation, repeated oral or topical administration, and administration via subcutaneous minipump. As non-limiting examples, an α-2A/α-1A selective agonist or pharmaceutical composition of the invention can be peripherally and chronically administered by continuous intravenous administration via implanted infusion minipump, or using an extended release formulation.

It is understood that slow-release formulations can be useful for preventing or alleviating chronic pain or another chronic condition such as, without limitation, a chronic neurodegenerative condition. It is further understood that the frequency and duration of dosing of such a slow-release formulation will be dependent, in part, on the prevention or extent of alleviation desired and the half-life of the α-2A/α-1A selective agonist, and that a variety of routes of administration are useful for delivering slow-release formulations, as discussed hereinabove.

An α-2A/α-1A selective agonist or ophthalmic composition of the invention can be peripherally administered to a subject to prevent or alleviate an ocular condition by any of a variety of means depending, in part, on the characteristics of the selective agonist to be administered and the history, risk factors and symptoms of the subject. Peripheral routes of administration suitable for preventing or alleviating an ocular condition include both systemic and local administration. In particular embodiments, an ophthalmic composition containing an α-2A/α-1A selective agonist is administered topically such as by ocular drops, or by local injection, or is released from an intraocular or periocular implant.

Systemic and local routes of administration useful in preventing or alleviating an ocular condition by administration of an α-2A/α-1A selective agonist or ophthalmic composition of the invention encompass, without limitation, oral gavage; intravenous injection; intraperitoneal injection; intramuscular injection; subcutaneous injection; transdermal diffusion and electrophoresis; topical eye drops and ointments; periocular and intraocular injection including subconjunctival injection; extended release delivery devices such as locally implanted extended release devices; and intraocular and periocular implants including bioerodible and reservoir-based implants.

In one embodiment, an ophthalmic composition containing an α-2A/α-1A selective agonist is administered topically to the eye. The α-2A/α-1A selective agonist can be administered, for example, as part of an ophthalmic solution such as ocular drops. In another embodiment, an ophthalmic composition containing an α-2A/α-1A selective agonist of the invention is injected directly into the eye. In a further embodiment, an ophthalmic composition containing an α-2A/α-1A selective agonist of the invention is released from an intraocular or periocular implant such as a bioerodible or reservoir-based implant.

As indicated above, an ophthalmic composition containing an α-2A/α-1A selective agonist can be administered locally via an intraocular or periocular implant, which can be, without limitation, bioerodible or reservoir-based. As used herein, the term "implant" refers to any material that does not significantly migrate from the insertion site following implantation. An implant can be biodegradable, non-biodegradable, or composed of both biodegradable and non-biodegradable materials; a non-biodegradable implant can include, if desired, a refillable reservoir. Implants useful for preventing or alleviating an ocular condition include, for example, patches, particles, sheets, plaques, microcapsules and the like, and can be of any shape and size compatible with the selected site of insertion, which can be, without limitation, the posterior chamber, anterior chamber, suprachoroid or subconjunctiva of the eye. It is understood that a useful implant generally releases the implanted ophthalmic composition at a therapeutically effective dose to the eye of the subject over an extended period of time. A variety of ocular implants and extended release formulations suitable for ocular release are well known in the art, as described, for example, in U.S. Pat. Nos. 5,869,079 and 5,443,505.

The following examples are intended to illustrate but not limit the present invention.

EXAMPLE I

Preparation of Compound 1

This example describes preparation of the α-2A/α-1A selective agonist, Compound 1.

A. Preparation of Compound 1 ((+)-(S)-4-[1-(2,3-dimethyl-phenyl)-ethyl]-1,3-dihydro-imidazole-2-thione)

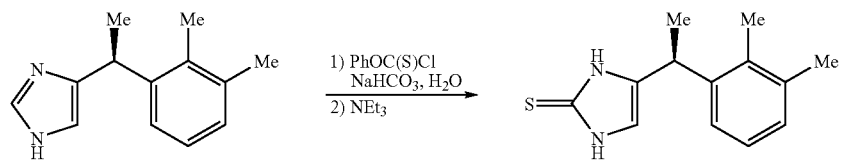

dexmeditomidine                    Compound 1

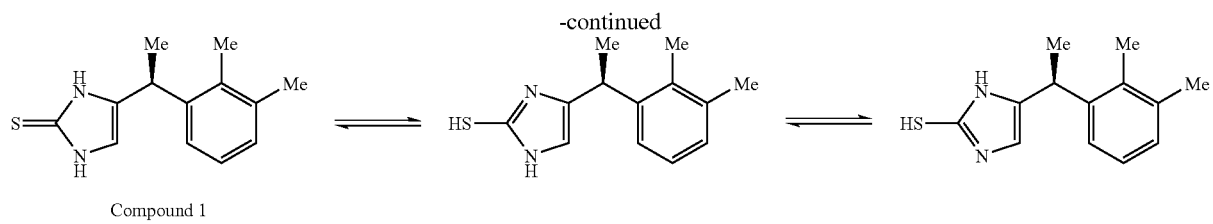

Compound 1

A mixture of (+)-(S)-4-[1-(2,3-dimethyl-phenyl)-ethyl]-1H-imidazole (dexmeditomidine; 2.00 g, 10.0 mmol) prepared as described in Cordi et al., *Synth. Comm.* 26: 1585 (1996), in THF (45 mL) and water (40 mL) was treated with $NaHCO_3$ (8.4 g, 100 mmol) and phenylchlorothionoformate (3.7 mL, 27.4 mmol). After stirring for four hours at room temperature, the mixture was diluted with water (30 mL) and ether (75 mL). The organic layer was removed, and the aqueous layer extracted twice with a 50 ml volume or ether. The organic layers were dried over $MgSO_4$ and filtered. The residue was concentrated under vacuum, diluted with MeOH (54 mL) and reacted with $NEt_3$ (6.5 mL) at room temperature for 16 hours. The solvent was removed under vacuum and replaced with 30% $CH_2C_{12}$:hexane. The solvent was removed again and solids formed. After further resuspension in 30% $CH_2C_{12}$:hexane, the solid was collected on a filter, washed with $CH_2C_{12}$:hexane and dried under vacuum to give Compound 1 ((+)-(S)-4-[1-(2,3-dimethyl-phenyl)-ethyl]-1,3-dihydro-imidazole-2-thione) 1.23 g (53%). A schematic of the preparation of Compound 1 is shown above.

Characterization of the product yielded the following. Optical rotation: $[a]_D20+14°$ (c 1.25 in MeOH). $1^H$ NMR: (300 MHz, DMSO) d 11.8 (s, 1H), 11.6 (s, 1H), 7.03-7.01 (m, 2H), 6.95-6.91 (m, 1H), 6.50 (s, 1H), 4.15 (q, J=6.9 Hz, 1H), 2.25 (s, 3H), 2.20 (s, 3H), 1.38 (d, J=6.9 Hz, 3H).

B. Procedure for the Preparation of Compound 2 (5-(1H-Imidazol-4-ylmethyl)-cyclohex-1-enyl]-methanol)

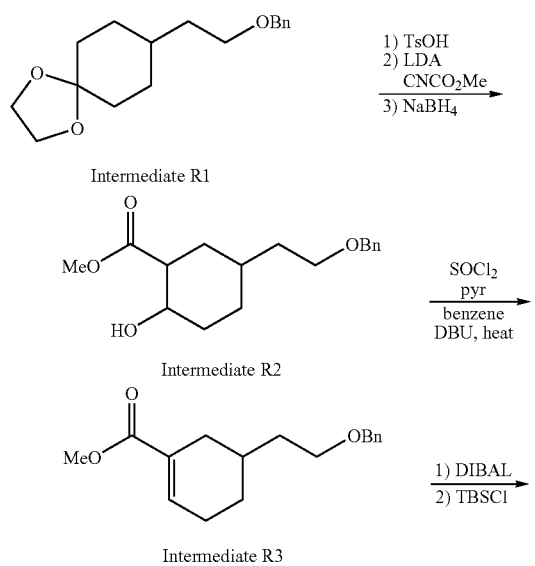

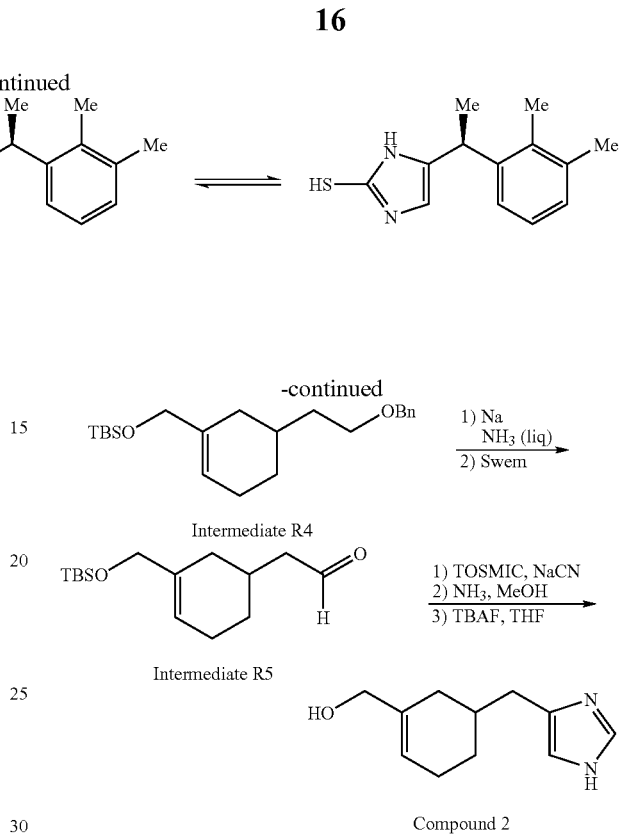

Compound 2

8-(2-Benzyloxy-ethyl)-1,4-dioxa-spiro[4.5]decane (Intermediate R1; 1.02 g, 3.70 mmol) was prepared as described in Ciufolini et al., *J. Amer. Chem. Soc.* 113: 8016 (1991). This compound was dissolved in acetone (100 mL):$H_2O$ (5 mL) and reacted with TsOH (140 mg, 0.74 mmol) at 45° C. for 5 hours. After a standard aqueous work-up the material was purified by chromatography on $SiO_2$ to give 4-(2-benzyloxy-ethyl)-cyclohexanone as a colorless oil (97%).

A solution of LDA (33 ml, 1.5 M in $Et_2O$) in THF (50 mL) at −78° C. was treated with 4-(2-benzyloxy-ethyl)-cyclohexanone (9.5 g, 40.2 mmol). The mixture was warmed to 0° C. over 30 minutes before re-cooling to −78° C. and adding HMPA (7 mL). Methyl cyanoformate (4.1 mL, 85 mmol) was added, and the mixture stirred for 15 minutes before aqueous quench and work-up. The product was purified by chromatography on $SiO_2$ with 10% EtOAc:Hx. 5-(2-Benzyloxy-ethyl)-2-oxo-cyclohexanecarboxylic acid methyl ester was isolated, 5.8 g (49%), and reduced with an equivalent of $NaBH_4$ in MeOH at −10° C. The alcohol. (Intermediate R2 above) was purified by chromatography on $SiO_2$ with 30 to 50% EtOAC:Hx. (~90% yield).

A solution of 5-(2-benzyloxy-ethyl)-2-hydroxy-cyclohexanecarboxylic acid methyl ester (Intermediate R2; 0.72 g, 2.48 mmol) in pyridine (10 mL) was treated with $SOCl_2$ (0.73 mL, 12.4 mmol) at −20° C. The mixture was allowed to react for 15 minutes and was then warmed to 55° C. for 16 hours. The solvents were removed under vacuum and the residue was diluted in ether at 0° C. The solution was quenched with water, washed with 1M HCl, 5% NaOH and brine. The organic material was dried over $MgSO_4$, filtered and freed of solvent. The mixture was diluted with benzene, and water was removed by azeotropic distillation under vacuum. The residue was dissolved in benzene (15 mL), and DBU (0.76 mL, 5 mmol) was added). The mixture was reacted for 30 minutes at room temperature. After work-up and chromatography on SiO$_2$ with 20% EtOAc:Hx, 5-(2-benzyloxy-ethyl)-cyclohex-1-enecarboxylic acid methyl ester (Intermediate R3) was isolated (0.56 g (82%)).

Intermediate R3 was dissolved in THF (100 mL) and added to a solution of DIBAL (70 mL, 1M in hexanes) in THF (160 mL) at −35° C. for 35 minutes. The mixture was quenched with Rochelle's salt solution, and extracted with ether. The dried residue was purified by chromatography on SiO$_2$ with 30% EtOAc:Hx to yield [5-(2-benzyloxy-ethyl)-cyclohex-1-enyl]-methanol 4.6 g (80%). A solution of the alcohol (4.0 g, 18.7 mmol) in DMF (60 mL) was treated with triethylamine (3 mL) followed by TBSCl (3.0 g, 22.4 mol) for 20 minutes at room temperature. The residue was isolated from an aqueous work-up and purified by chromatography to give [5-(2-benzyloxy-ethyl)-cyclohex-1-enyl-methoxy]-tert-butyl-dimethyl-silane (Intermediate R4) 3.6 g (63%).

The benzyl protected alcohol (Intermediate R4) (2.0 g, 5.55 mmol) in THF (20 mL) was cooled to −70° C., and NH$_3$ was condensed in this flask (~20 mL). Na chunks were added, and the mixture was allowed to stir at −70° C. for 15 minutes. The mixture was warmed to −30° C. for 20 minutes, quenched with NH$_4$Cl and isolated by extraction. The residue was purified by chromatography on SiO$_2$ with 25% EtOAc:Hx (99%). The alcohol was oxidized by the standard "Swern" protocol. The alcohol 2-[3-(tert-butyl-dimethyl-silanyloxymethyl)-cyclohex-3-enyl]-ethanol (1.8 g, 4.8 mmol) was added to a solution of oxalyl chloride (3.55 mL, 7.1 mmol) in CH$_2$Cl$_2$ (30 mL) with DMSO (0.63 mL, 8.9 mmol) at −78° C. After 40 minutes, NEt$_3$ (2.51 mL) was added, and the mixture was warmed to room temperature. After standard aqueous work-up and purification, [3-(tert-butyl-dimethyl-silanyloxymethyl)-cyclohex-3-enyl]-acetaldehyde (Intermediate R5) was isolated (~95%).

The following preparation followed the procedure by Horne et al., *Heterocycles* 39:139 (1994). A solution of the aldehyde (Intermediate R5; 0.34 g, 1.3 mmol) in EtOH (5 mL) was treated with tosylmethyl isocyanide (TosMIC; Aldrich; 0.25 g; 1.3 mmol) and NaCN (~15 mg, cat) and allowed to stir at room temperature for 20 minutes. The solvent was removed in vacuo; the residue was dissolved in ~7M NH$_3$ in MeOH and transferred to a resealable tube before heating at 100° C. for 15 hours. The mixture was concentrated and purified by chromatography on SiO$_2$ with 5% MeOH (sat. w/NH$_3$):CH$_2$Cl$_2$. A solution of the product in THF with TBAF (1.5 eq.) was stirred at room temperature after aqueous workup. The crude product was chromatographed (5-7% NH$_3$/MeOH in CH$_2$Cl$_2$) and designated Compound 2.

Characterization of Compound 2 yielded the following. $^1$H NMR (300 MHz, DMSO-d$^6$) d 7.52 (s, 1H), 6.72 (s, 1H), 5.54 (brs, 1H), 3.73 (s, 2H), 2.46 (d, J=6 Hz, 2H), 1.5-2.1 (m, 6H), 1.0-1.55 (m, 1H)

EXAMPLE II

Characterization of an α-2 Agonist with Greater α-2A/α-1A Functional Selectivity than Brimonidine This example demonstrates that α-2A/α-1A selectivity in receptor proximal functional assays correlates with non-sedating in vivo activity.

A. In Vitro Functional Assays

Proximal functional activity at the α-1A and α-2A adrenergic receptors was compared for brimonidine, dexmeditomidine, Compound 1 and Compound 2. Brimonidine was obtained from Sigma; dexmeditomidine was prepared as described in Cordi et al., supra, 1996; and Compounds 1 and 2 were synthesized as described in Example I above. The α-adrenergic receptor pharmacological profiles were analyzed in assays using cell lines stably expressing α-2A or α-1A receptors, described below.

To assess α-1A activity, compounds were functionally tested for the ability to stimulate an increase in intracellular calcium in HEK293 cells stably expressing bovine α-1A receptor. α-1A relative efficacy was determined in reference to the full agonist, phenylephrine, as described below. As summarized in Table 1 shown above, dexmeditomidine and Compound 2 had α-1A relative efficacies greater than that of brimonidine, while the α-1A relative efficacy of Compound 1 was so low as to be undetectable in this assay.

The same compounds were also functionally assayed for proximal α-2A function by assaying for inhibition of forskolin-induced cAMP accumulation in PC12 cells stably expressing human α-2A receptor. Intracellular cAMP levels were determined using the Biotrak cAMP enzyme immunoassay system described below. The EC$_{50}$ for α-2A cAMP inhibition was expression as a ratio with the α-1A EC$_{50}$ to give an α-1A/α-2A potency ratio. As shown in Table 1 above, the α-2 adrenergic agonist denoted Compound 1 was highly α-2A/α-1A selective, as evidenced by the undetectable level of α-1A activity observed for this compound. In contrast, dexmeditomidine, for example, was less α-2A/α-1A selective than was brimonidine. These results indicate that Compound 1 is highly selective for activation of the α-2A receptor as compared to the α-1A receptor.

Stable cell lines expressing an adrenergic receptor were established as follows. The bovine α-1A, hamster α-1B, human α-2A and human α-2C receptor cDNAs were blunt-end subcloned into the NheI-EcoRI sites in the retroviral vector pCL BABE Puro. The retroviral constructs were verified by double stranded DNA sequencing. High titer pseudotyped retroviral particles were produced by co-transfecting HEK293GP, a HEK293 cell line stably expressing Gag-Pol of the Maloney leukemia virus, with the appropriate retroviral vector and pMD.G, an expression vector for the vesicular stomatitis virus envelope protein, VSV-G. Sixteen hours after transfection, the media (DMEM, 10% FCS) was changed; the high titer (~1×106 pfu/mL) media was then harvested forty-eight hours later. The supernatant was filtered through a 0.4 μM filter.

The human α-2A receptor supernatant was added, in varying amounts, to naive PC12 cells, which were then incubated for 48 hours. The transduced cell population was replated at a lower, density and grown in media containing 100 μg/ml puromycin. Non-transduced cells were killed within three days, and single foci grew within two months. The foci were picked, expanded, and assayed for receptor density by brimonidine radioligand binding. Functional α-2 receptor activity was confirmed by inhibition of forskolin-induced cAMP accumulation.

The bovine α-1A receptor supernatant was added, in varying amounts, to naive HEK293 cells, which were then incubated for 48 hours. The transduced cell population was replated at a lower density and grown in media containing 0.25 μg/ml puromycin. Significant cell death was evident within three days, with single foci appearing within two weeks. After the foci were picked and expanded, subclones were functionally assayed for α-1 receptor expression by measuring phenylephrine-induced intracellular Ca$_{+2}$ accumulation as described below. Receptor density was measured in a prazosin radioligand binding assay.

Intracellular $Ca_{+2}$ responses were measured in HEK293 cells stably expressing the bovine α-1A adrenergic receptor. Between 40,000 to 50,000 cells were plated per well in 96-well poly-D-lysine coated plates in 0.2 ml DMEM containing 10% heat-inactivated fetal calf serum, 1% antibiotic-antimycotic and 0.25 g/ml puromycin one day prior to use. Cells were washed twice with HBSS supplemented with 10 mM HEPES, 2.0 mM $CaCl_2$ and 2.5 mM probenicid, and subsequently incubated at 37° C. for 60 minutes with 4 M Fluo-4 (Molecular Probes; Eugene, Oreg.). Extracellular dye was washed from the plates twice prior to placing the plates in the fluorometric imaging plate reader (FLIPR; Molecular Devices; Sunnyvale, Calif.) Compounds to be assayed were diluted in HBSS and aliquoted into a 96-well microplate; compounds were tested over the concentration range of 0.64 nM to 10,000 nM. Data for $Ca_{+2}$ responses were obtained in arbitrary fluorescence units.

The percent α-1A efficacy (% E) was determined by comparing the maximum effect of each agonist to the maximum effect of the standard full agonist phenylephrine. The values represent the mean and SEM from 3-15 independent experiments. The fold-selectivity of the agonists for α-2 receptors relative to α-1 receptors was calculated from the ratio of their mean $EC_{50}$s for activating the α-1A and α-2A receptors.

Intracellular cAMP measurement was performed as follows. PC12 cells stably expressing the human α-2A adrenergic receptor were plated in 96-well poly-D-lysine coated plates at a density of 30,000 cells per well in 100 μl DMEM supplemented with 10% horse serum, 5% heat inactivated fetal bovine serum, 1% antibiotic-antimycotic and 100 μg/ml puromycin. Cells were grown overnight at 37° C. and 5% $CO_2$. Cells were dosed by adding an equal volume of media containing IBMX (to a final concentration of 1 mM), forskolin (to a final concentration of 10 M) and the appropriate drug dilution (to a final concentration of between 10-5 M and 10-12 M). After a 10 minute incubation, media was aspirated, and the cells lysed with 200 μl lysis buffer (Amersham Biosciences; Piscataway, N.J.). Plates were stored at −20° C. for up to 24 hours prior to assay. Intracellular cAMP was determined using the Biotrak cAMP enzyme immunoassay system (Amersham Biosciences) according to the manufacturer's instructions. Plates were read on a plate reader at 450 nm.

Dose response curves for in vitro assays were generated using KaleidaGraph (Synergy Software; Reading, Pa.) by least squares fits to the equation, response=maximum response+((minimum response−maximum response)/(1+ (concentration of ligand/$EC_{50}$)). The percent α-1A efficacy was determined by comparing the maximum effect of the compound to the effect of the standard full agonist phenylephrine.

B. In Vivo Efficacy and Sedative Effects

In addition to the cell-based assays described above, the various α-2 agonists were assayed for the ability to alleviate sulprostone-induced tactile hypersensitivity and for sedating activity at various doses. The tactile hypersensitivity of 5-6 mice per group was scored every five minutes between 15 and 50 minutes following intraperitoneal dosing. Vehicle treated animals typically had a score of about 4. In addition, the locomoter activity of 5-6 mice per group was measured in a five minute period 30 minutes following intraperitoneal dosing. Locomoter activity relative to vehicle-treated animals was expressed as a percentage; percentage sedation was calculated as 100% minus the percent locomoter activity.

As shown in FIG. 2 (upper left panel), brimonidine was approximately 60% sedating at a dose 10-fold greater than the 100 μg/kg dose which gave a 50% reduction in sulprostone sensitization. Furthermore, dexmeditomidine, shown in the upper right panel of FIG. 2, was completely sedating at a dose 10-fold greater than the dose required to produce a 50% reduction in sensitization score. In contrast, Compound 1 administered orally at a dose of 1 μg/kg, produced a 50% reduction in the sensitization score (solid line, left axis) with less than 30% sedation (open diamond, right axis) at doses 100-fold and even 1000-fold greater than the 1 μg/kg dose (see FIG. 2, lower left panel). Similar results were observed following intraperitoneal administration of Compound 1. Intraperitoneal administration of Compound 2 also produced more than a 50% reduction in the sensitization score at 10 μg/kg (solid line, left axis) with less than 30% sedation at a 10-fold greater dose. Thus, Compound 1, which had an extremely low (undetectable) α-1A relative efficacy, alleviated tactile hypersensitivity without concomitant sedation upon peripheral administration. Similarly, Compound 2, which has an α-1A/α-2A potency ratio greater than that of brimonidine, also alleviated tactile hypersensitivity without concomitant sedation upon peripheral administration.

In vivo experiments were performed as follows. Sulprostone (Cayman Chemical; Ann Arbor, Mich.) was dissolved in dimethyl sulfoxide (DMSO), and brimonidine, phenylephrine, and clonidine were obtained from Sigma (St. Louis, Mo.) and dissolved in saline. Spinal drug injections were performed as follows. Mice (20-30 μg) were injected intrathecally as described in Hylden and Wilcox, Eur. J. Pharmacol. 67:313-316 (1980). Briefly, a sterile 30-gauge ½ inch needle attached to a microsyringe was inserted between the L5 and L6 vertebrae. The mouse was held firmly by the pelvic girdle in one hand, while the syringe was held in the other hand at an angle of approximately 20° above the vertebral column. The needle was inserted into the tissue to one side of the L6 spinous process, into the groove between the spinous and transverse processes. The needle angle was decreased to about 10°, and the needle slowly advanced forward into the intervertebral space until a pop was felt and there was a visible serpentine tail movement. Compounds were slowly injected in the subarachnoid space in a volume of 5 μl. Each compound was tested at multiple doses. The minimal efficacious dose was used for all subsequent experiments.

Sensitivity to light touch was quantified by scoring the response of mice to light stroking of their flanks with a small paintbrush, which is not normally painful. The mice were rated on the following scale once every 5 minutes between 15 and 50 minutes post injection: a score of "2" was given to animals showing aggressive escape responses along with squeaking and biting at the brush; a score of "1" was given to animals exhibiting mild squeaking with attempts to escape; and a score of "0" was given if the animal showed no response to the light stroking of the paintbrush. The scores were summed to generate a cumulative score of 0 to 16 as described in Minami et al., Pain 57:217-223 (1994). Statistical calculations of significance for in vivo studies were done using a two-tailed Student's t-test.

In sum, these results indicate that α-2A/α-1A adrenergic receptor functional selectivity of α-2 agonists in in vitro cell-based functional assays is associated with lack of sedative activity at the therapeutic dose following systemic or other peripheral dosing. These results further indicate that Compound 1, which exhibits an α-2A/α-1A adrenergic receptor in vitro functional selectivity better than the selectivity off brimonidine, is a particularly useful α-2 agonist due to the lack of in vivo sedative effects at therapeutic doses.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

We claim:

1. A method of treating diabetic neuropathic pain comprising administering a compound of the formula

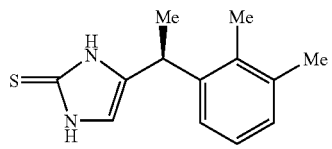

or a pharmaceutically acceptable salt thereof,
to a mammal in need thereof.

2. A method of treating fibromyalgic pain comprising administering a compound of the formula

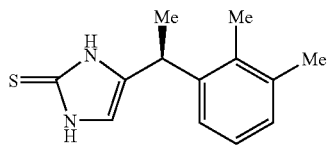

or a pharmaceutically acceptable salt thereof,
to a mammal in need thereof.

3. A method of treating pain associated with irritable bowel syndrome comprising administering a compound of the formula

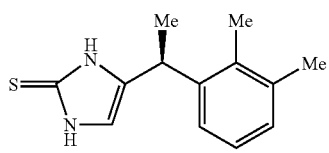

or a pharmaceutically acceptable salt thereof,
to a mammal in need thereof.

* * * * *